United States Patent
Shimizu et al.

(10) Patent No.: US 6,897,299 B2
(45) Date of Patent: May 24, 2005

(54) PROCESS FOR PRODUCING ERYTHROMYCIN DERIVATIVE

(75) Inventors: Hitoshi Shimizu, Tokyo (JP); Kaname Tsuzaki, Tokyo (JP); Mitsuhiro Kurita, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/363,318

(22) PCT Filed: Aug. 31, 2001

(86) PCT No.: PCT/JP01/07534

§ 371 (c)(1), (2), (4) Date: Mar. 3, 2003

(87) PCT Pub. No.: WO02/18403

PCT Pub. Date: Mar. 7, 2002

(65) Prior Publication Data

US 2003/0195343 A1 Oct. 16, 2003

(30) Foreign Application Priority Data

Sep. 1, 2000 (JP) ........................ 2000-265277

(51) Int. Cl.$^7$ ................................. C07H 1/00
(52) U.S. Cl. ........................ 536/7.2; 536/18.5
(58) Field of Search ................ 536/7.2, 18.5, 536/7.4

(56) References Cited

U.S. PATENT DOCUMENTS

| | | |
|---|---|---|
| 3,736,313 A | 5/1973 | Jones et al. |
| 5,658,888 A | 8/1997 | Koga et al. |
| 5,959,088 A * | 9/1999 | Miura et al. .......... 536/7.2 |
| 6,046,171 A * | 4/2000 | Or et al. ............... 514/29 |

FOREIGN PATENT DOCUMENTS

| | | |
|---|---|---|
| EP | 0215355 | 3/1987 |
| EP | 0846697 | 6/1998 |
| JP | 01-203398 | 8/1989 |

OTHER PUBLICATIONS

Tadanier, et al. *Some Chemical and Stereochemical Modifications of the Erythromycin Lactone Rings*, Journal of Organic Chemistry, vol. 39, No. 17 (1974), pp. 2495–2501.

* cited by examiner

*Primary Examiner*—Elli Peselev
(74) *Attorney, Agent, or Firm*—Browdy and Neimark, P.L.L.C.

(57) ABSTRACT

A method for preparing a fumarate salt of a compound represented by Formula (II):

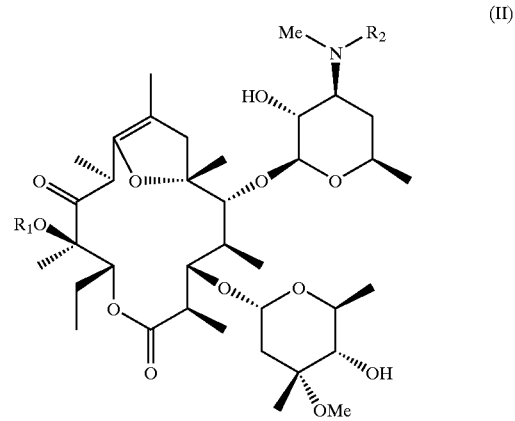

(wherein $R_1$ represents a hydrogen atom or a lower alkyl group, and $R_2$ represents a lower alkyl group), which comprises carbamating a compound represented by Formula (I):

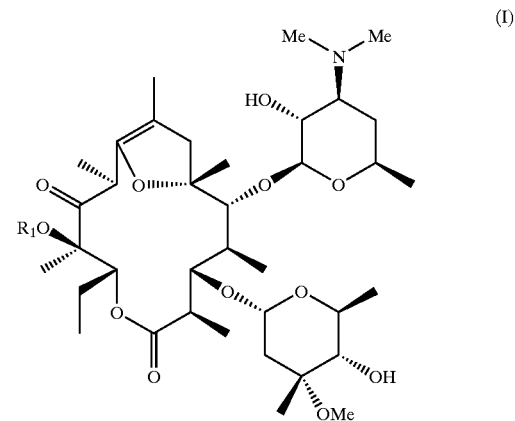

(wherein $R_1$ represents a hydrogen atom or a lower alkyl group), removing all carbamate groups from this compound, alkylating the nitrogen atom at the 3'-position of the desosamine ring in the resulting compound to give the compound represented by Formula (II), and converting this compound into a fumarate salt, wherein the compound represented by Formula (I) is carbamated in the presence of a cyclic ether or a carboxylic ester. This method enables efficient preparation of high-quality erythromycin derivatives.

25 Claims, No Drawings

PROCESS FOR PRODUCING ERYTHROMYCIN DERIVATIVE

TECHNICAL FIELD

The present invention relates to a method for preparation of erythromycin derivatives.

BACKGROUND ART

The compound represented by Formula (II):

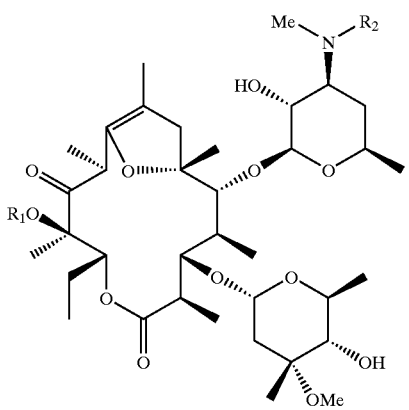

(wherein $R_1$ represents a hydrogen atom or a lower alkyl group, and $R_2$ represents a lower alkyl group) is described in, for example, JP 6-56873 A and JP 9-100291 A. These compounds are known to have the ability to enhance movement of the digestive tract.

Methods for preparation of this compound are found in, for example, JP 6-56873 A, Bioorg. & Med. Chem. Lett., vol. 4(11), 1347 (1994) and JP 9-100291 A.

However, the preparation methods found in JP 6-56873 A and Bioorg. & Med. Chem. Lett., vol. 4(11), 1347 (1994) are difficult to implement for industrial purposes because they involve many steps and repeatedly use column chromatography for purification. JP 9-100291 A teaches an improved method for preparing the compound of the present invention, represented by Formula (II):

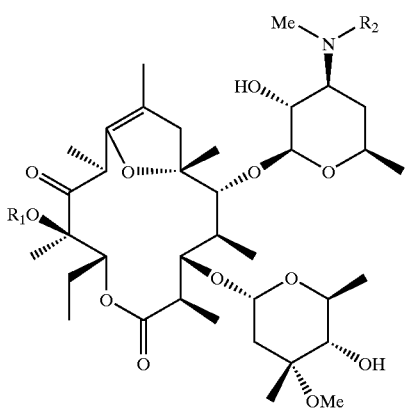

(wherein $R_1$ represents a hydrogen atom or a lower alkyl group, and $R_2$ represents a lower alkyl group), which overcomes the above problems associated with the preparation methods found in JP 6-56873 A and Bioorg. & Med. Chem. Lett., vol. 4(11), 1347 (1994). This publication discloses a method in which a compound corresponding to Compound 5 of the present invention is carbamated in the presence of toluene to prepare a compound corresponding to Compound 6 of the present invention. It also discloses a method in which a compound corresponding to Compound 6 of the present invention is catalytically hydrogenated under a hydrogen atmosphere using a palladium-carbon catalyst to prepare a compound corresponding to Compound 7 of the present invention. Further, it discloses a method in which a compound corresponding to Compound 8 of the present invention is dissolved in methanol together with fumarate and then crystallized by addition of isopropanol to prepare crystals of a fumarate salt of Compound 8 according to the present invention. Furthermore, it discloses a method in which crystals of a fumarate salt of Compound 8 according to the present invention are dissolved in methanol, followed by addition of isopropanol to prepare purified crystals of a fumarate salt of Compound 8 according to the present invention.

DISCLOSURE OF THE INVENTION

Starting with a compound corresponding to Compound 5 of the present invention, carbamation in the solvent described in JP 9-100291 A involves a problem of slow reaction and extended time for completion of the reaction and also involves a problem of complicated and inefficient procedures because the solvent should be replaced by a water-immiscible solvent such as ethyl acetate to extract a reaction product, i.e., a compound corresponding to Compound 6 of the present invention. Likewise, in a case where a compound corresponding to Compound 6 of the present invention is catalytically hydrogenated under a hydrogen atmosphere using a palladium-carbon catalyst, this method involves a problem that the reaction product may be decomposed because the reaction mixture becomes acidic during the reaction. Further, in a case where a compound corresponding to Compound 8 of the present invention is dissolved in methanol together with fumarate and then crystallized by addition of isopropanol, this method involves a problem that the resulting crystals are difficult to dry and highly impure. Furthermore, in a case where crystals of a fumarate salt of a compound corresponding to Compound 8 of the present invention are dissolved in methanol, followed by addition of isopropanol to prepare crystals of a fumarate salt of a compound corresponding to Compound 8 of the present invention, this method involves a problem that the resulting crystals are difficult to dry and highly impure.

The present invention was made in view of the problems stated above and aims to provide an efficient method for preparing erythromycin derivatives. It also aims to provide a method for preparing erythromycin derivatives of high quality.

As a result of extensive and intensive efforts made to achieve the above aims, the inventors of the present invention found an efficient method for preparing erythromycin derivatives and completed one aspect of the present invention. Also, the inventors of the present invention found a method for preparing erythromycin derivatives of high quality and completed another aspect of the present invention.

Namely, the present invention relates to a method for preparing a fumarate salt of a compound represented by Formula (II):

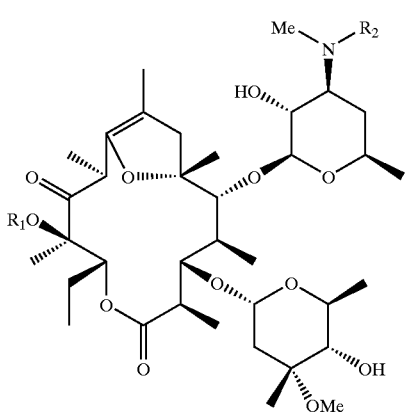

(wherein R₁ represents a hydrogen atom or a lower alkyl group, and R₂ represents a lower alkyl group), which comprises:

carbamating a compound represented by Formula (I):

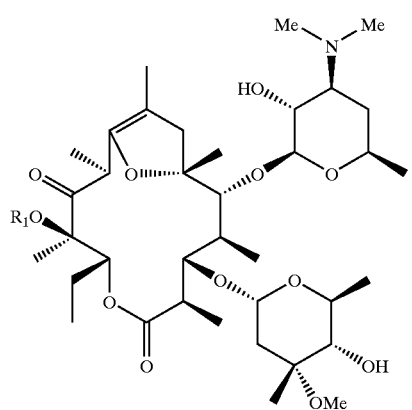

(wherein R₁ represents a hydrogen atom or a lower alkyl group) to give a compound represented by Formula (III)

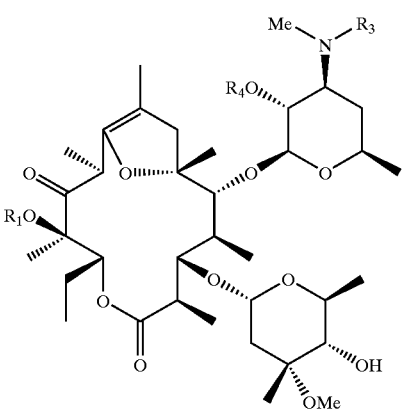

(wherein R₁ represents a hydrogen atom or a lower alkyl group, R₃ represents a carbamate group, and R₄ represents a hydrogen atom or a carbamate group);

removing all carbamate groups from the compound represented by Formula (III) to give a compound represented by Formula (IV):

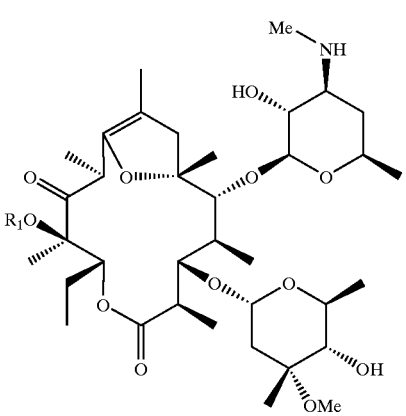

(wherein R₁ represents a hydrogen atom or a lower alkyl group);

alkylating the nitrogen atom at the 3'-position of the desosamine ring in the compound represented by Formula (IV) to give the compound represented by Formula (II); and converting the compound represented by Formula (II) into a fumarate salt;

wherein the compound represented by Formula (I) is carbamated in the presence of a cyclic ether or a carboxylic ester to give the compound represented by Formula (III).

The present invention also relates to a method for preparing a fumarate salt of a compound represented by Formula (II):

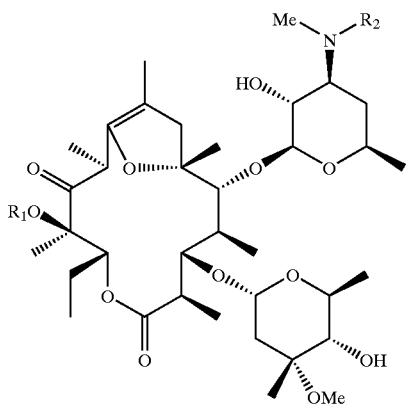

(wherein R₁ represents a hydrogen atom or a lower alkyl group, and R₂ represents a lower alkyl group), which comprises:

carbamating a compound represented by Formula (I):

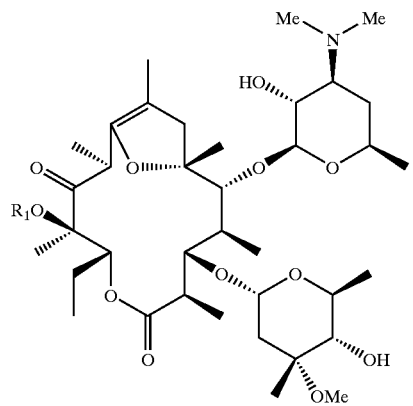

wherein $R_1$ represents a hydrogen atom or a lower alkyl group) to give a compound represented by Formula (III):

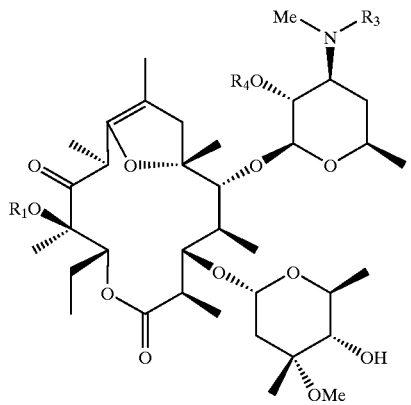

(III)

(wherein $R_1$ represents a hydrogen atom or a lower alkyl group, $R_3$ represents a carbamate group, and $R_4$ represents a hydrogen atom or a carbamate group);

removing all carbamate groups from the compound represented by Formula (III) to give a compound represented by Formula (IV):

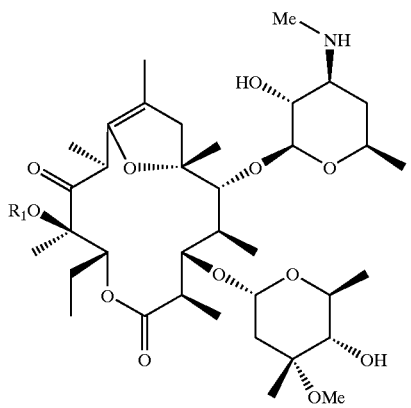

(IV)

(wherein $R_1$ represents a hydrogen atom or a lower alkyl group);

alkylating the nitrogen atom at the 3'-position of the desosamine ring in the compound represented by Formula (IV) to give the compound represented by Formula (II); and converting the compound represented by Formula (II) into a fumarate salt;

wherein the carbamate groups of the compound represented by Formula (III) are removed in the presence of sodium bicarbonate to give the compound represented by Formula (IV).

In addition, the present invention relates to a method for preparing a crystal of a fumarate salt of a compound represented by Formula (II):

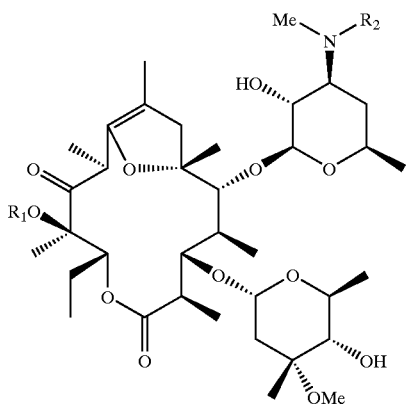

(II)

(wherein $R_1$ represents a hydrogen atom or a lower alkyl group, and $R_2$ represents a lower alkyl group), which comprises:

carbamating a compound represented by Formula (I):

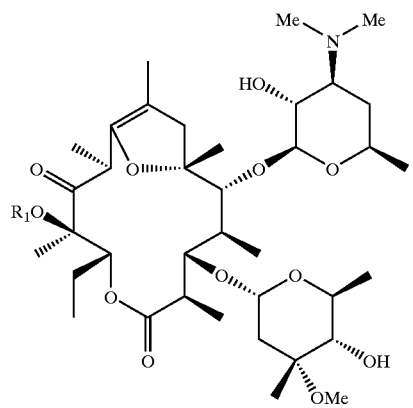

(I)

(wherein $R_1$ represents a hydrogen atom or a lower alkyl group) to give a compound represented by Formula (III):

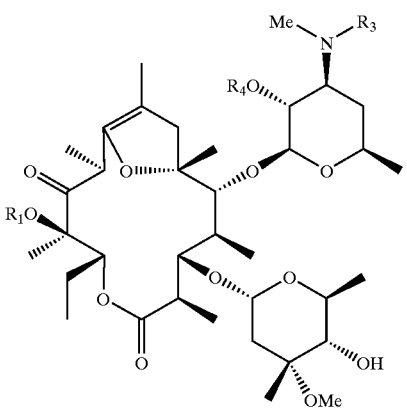

(III)

(wherein $R_1$ represents a hydrogen atom or a lower alkyl group, $R_3$ represents a carbamate group, and $R_4$ represents a hydrogen atom or a carbamate group);

removing all carbamate groups from the compound represented by Formula (III) to give a compound represented by Formula (IV):

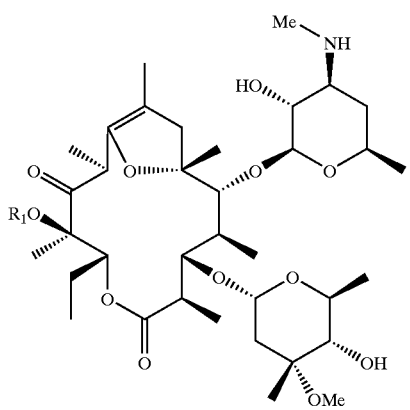

(wherein R₁ represents a hydrogen atom or a lower alkyl group);
alkylating the nitrogen atom at the 3'-position of the desosamine ring in the compound represented by Formula (IV) to give the compound represented by Formula (II);
converting the compound represented by Formula (II) into a fumarate salt to give a fumarate salt of the compound; and
crystallizing the fumarate salt from an alcohol-containing solvent;
wherein the crystal is obtained by crystallization from isopropanol.

Further, the present invention relates to a method for preparing a crystal of a fumarate salt of a compound represented by Formula (II):

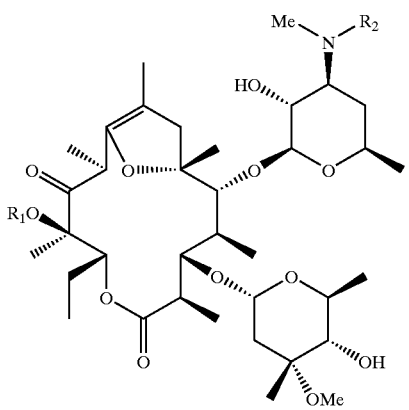

(wherein R₁ represents a hydrogen atom or a lower alkyl group, and R₂ represents a lower alkyl group), which comprises:
carbamating a compound represented by Formula (I):

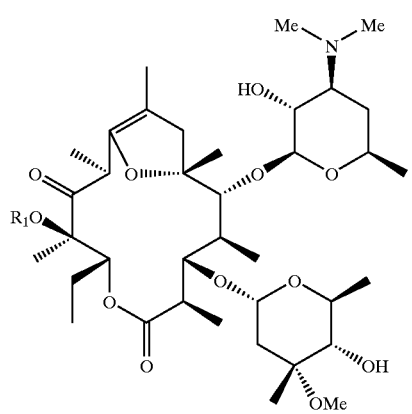

(wherein R₁ represents a hydrogen atom or a lower alkyl group) to give a compound represented by Formula (III):

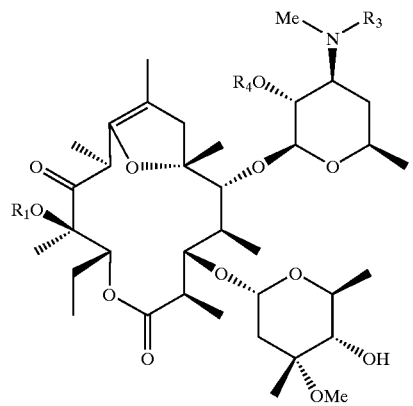

(wherein R₁ represents a hydrogen atom or a lower alkyl group, R₃ represents a carbamate group, and R₄ represents a hydrogen atom or a carbamate group);

removing all carbamate groups from the compound represented by Formula (III) to give a compound represented by Formula (IV):

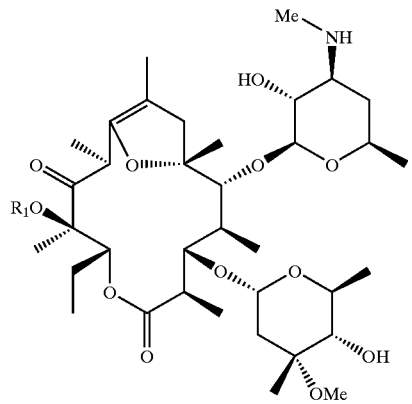

(wherein R₁ represents a hydrogen atom or a lower alkyl group);

alkylating the nitrogen atom at the 3'-position of the desosamine ring in the compound represented by Formula (IV) to give the compound represented by Formula (II);

converting the compound represented by Formula (II) into a fumarate salt to give a fumarate salt of the compound;

crystallizing the fumarate salt from an alcohol-containing solvent to give a crystal; and recrystallizing the crystal from an alcohol-containing solvent;

wherein the crystal is recrystallized from isopropanol.

Furthermore, the present invention relates to a method for preparing a crystal of a fumarate salt of a compound represented by Formula (II):

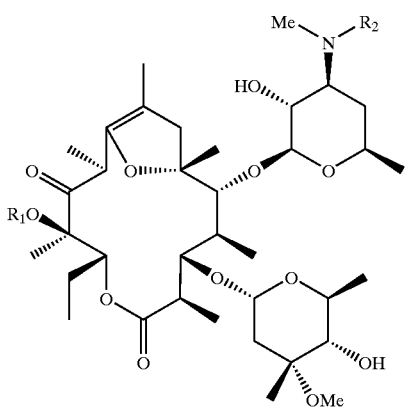

(II)

(wherein $R_1$ represents a hydrogen atom or a lower alkyl group, and $R_2$ represents a lower alkyl group), which comprises:

carbamating a compound represented by Formula (I):

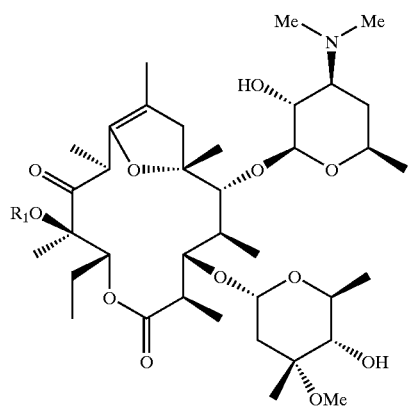

(I)

(wherein $R_1$ represents a hydrogen atom or a lower alkyl group) to give a compound represented by Formula (III):

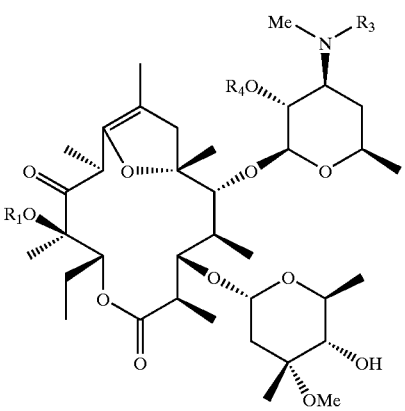

(III)

(wherein $R_1$ represents a hydrogen atom or a lower alkyl group, $R_3$ represents a carbamate group, and $R_4$ represents a hydrogen atom or a carbamate group);

removing all carbamate groups from the compound represented by Formula (III) to give a compound represented by Formula (IV):

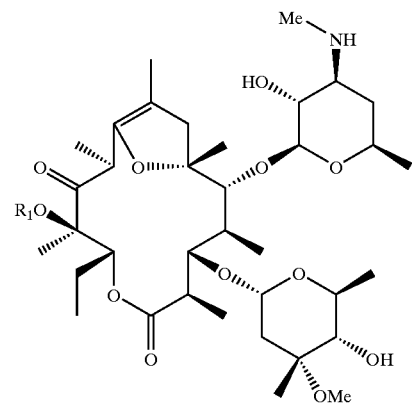

(IV)

(wherein $R_1$ represents a hydrogen atom or a lower alkyl group);

alkylating the nitrogen atom at the 3'-position of the desosamine ring in the compound represented by Formula (IV) to give the compound represented by Formula (II);

converting the compound represented by Formula (II) into a fumarate salt to give a fumarate salt of the compound;

crystallizing the fumarate salt from an alcohol-containing solvent to give a crystal; and recrystallizing the crystal from an alcohol-containing solvent;

wherein the crystal is recrystallized from isopropanol and then from a mixed methanol/isopropanol solvent.

The present invention also relates to a method for preparing a crystal of a fumarate salt of a compound represented by Formula (II):

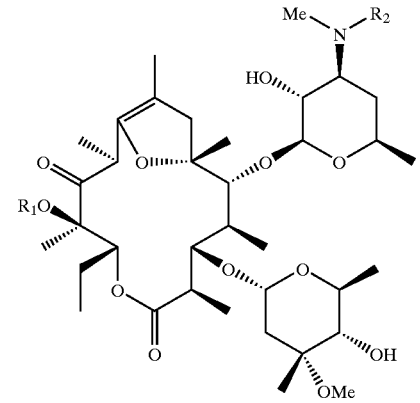

(II)

(wherein $R_1$ represents a hydrogen atom or a lower alkyl group, and $R_2$ represents a lower alkyl group), which comprises:

carbamating a compound represented by Formula (I):

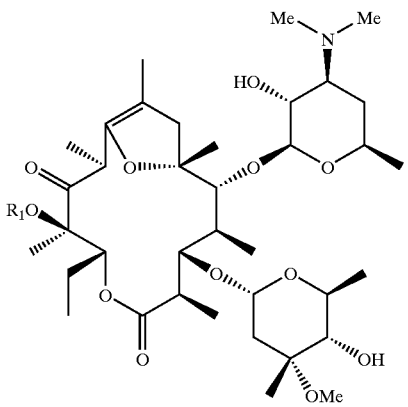
(I)

(wherein R₁ represents a hydrogen atom or a lower alkyl group) in the presence of a cyclic ether or a carboxylic ester to give a compound represented by Formula (III):

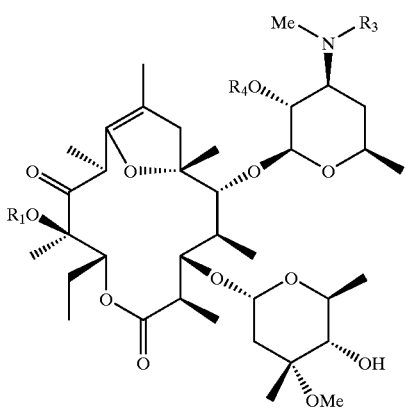
(III)

(wherein R₁ represents a hydrogen atom or a lower alkyl group, R₃ represents a carbamate group, and R₄ represents a hydrogen atom or a carbamate group);

removing all carbamate groups from the compound represented by Formula (III):

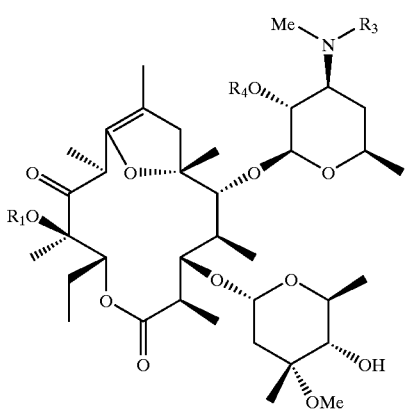
(III)

(wherein R₁ represents a hydrogen atom or a lower alkyl group, R₃ represents a carbamate group, and R₄ represents a hydrogen atom or a carbamate group) in the presence of sodium bicarbonate to give a compound represented by Formula (IV):

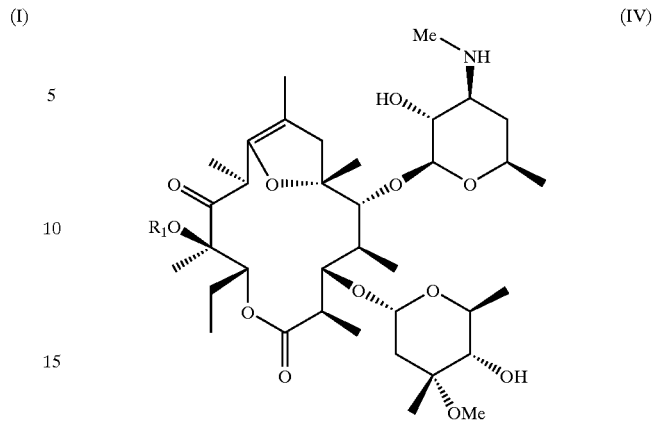
(IV)

(wherein R₁ represents a hydrogen atom or a lower alkyl group);

crystallizing a fumarate salt of the compound represented by Formula (II) from isopropanol to give a crystal of the fumarate salt of the compound; and recrystallizing the crystal from isopropanol and then from a mixed methanol/isopropanol solvent.

The present invention also relates to a method for preparing a compound represented by Formula (III):

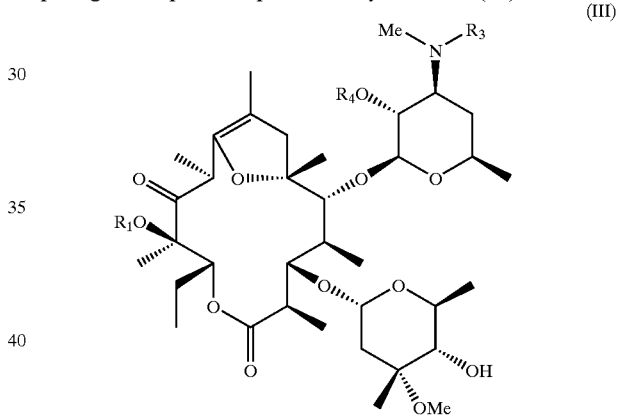
(III)

(wherein R₁ represents a hydrogen atom or a lower alkyl group, R₃ represents a carbamate group, and R₄ represents a hydrogen atom or a carbamate group), which comprises carbamating a compound represented by Formula (I):

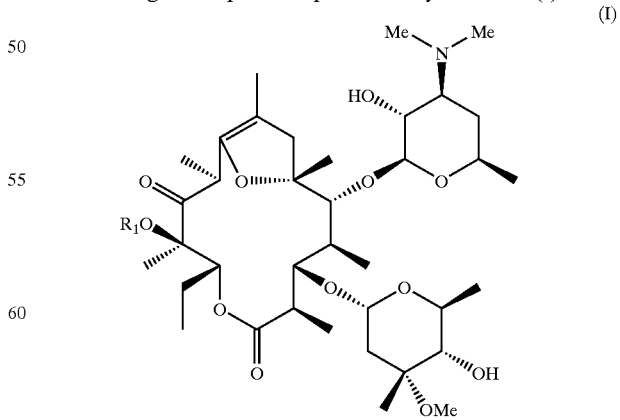
(I)

(wherein R₁ represents a hydrogen atom or a lower alkyl group) in the presence of a cyclic ether or a carboxylic ester.

In addition, the present invention relates to a method for preparing a compound represented by Formula (IV):

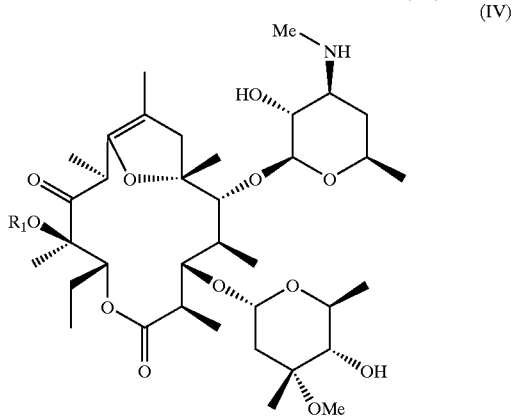

(wherein $R_1$ represents a hydrogen atom or a lower alkyl group), which comprises removing all carbamate groups from a compound represented by Formula (III):

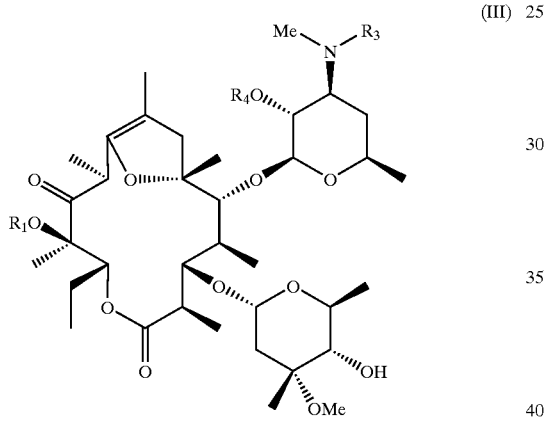

(wherein $R_1$ represents a hydrogen atom or a lower alkyl group, $R_3$ represents a carbamate group, and $R_4$ represents a hydrogen atom or a carbamate group) in the presence of sodium bicarbonate.

The present invention also relates to a method for preparing a crystal of a fumarate salt of a compound represented by Formula (II):

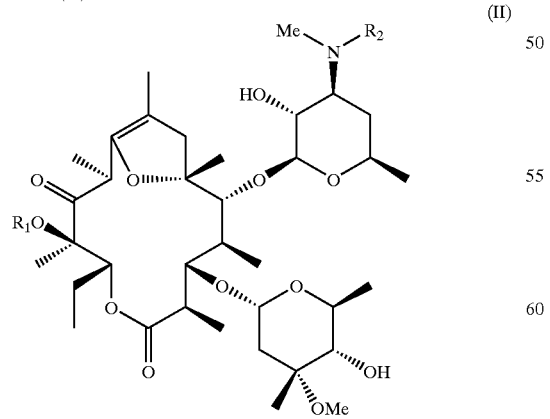

(wherein $R_1$ represents a hydrogen atom or a lower alkyl group, and $R_2$ represents a lower alkyl group), which comprises crystallizing a fumarate salt of the compound represented by Formula (II) from isopropanol.

In addition, the present invention relates to a method for preparing a crystal of a fumarate salt of a compound represented by Formula (II):

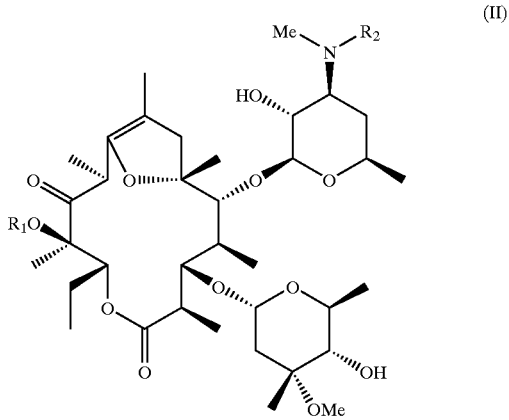

(wherein $R_1$ represents a hydrogen atom or a lower alkyl group, and $R_2$ represents a lower alkyl group), which comprises recrystallizing a crystal of a fumarate salt of the compound represented by Formula (II) from isopropanol.

Further, the present invention relates to a method for preparing a crystal of a fumarate salt of a compound represented by Formula (II):

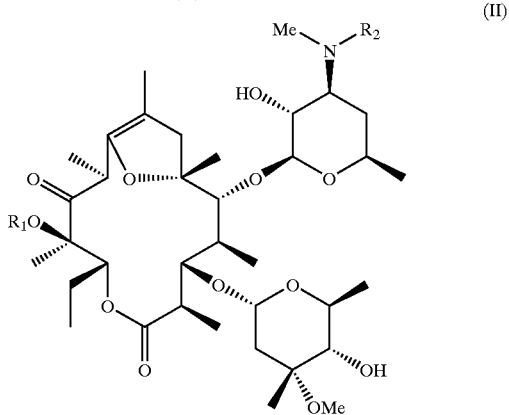

(wherein $R_1$ represents a hydrogen atom or a lower alkyl group, and $R_2$ represents a lower alkyl group), which comprises recrystallizing a crystal of a fumarate salt of the compound represented by Formula (II) from isopropanol and then from a mixed methanol/isopropanol solvent.

Furthermore, the present invention relates to a method for preparing a crystal of a fumarate salt of a compound represented by Formula (II):

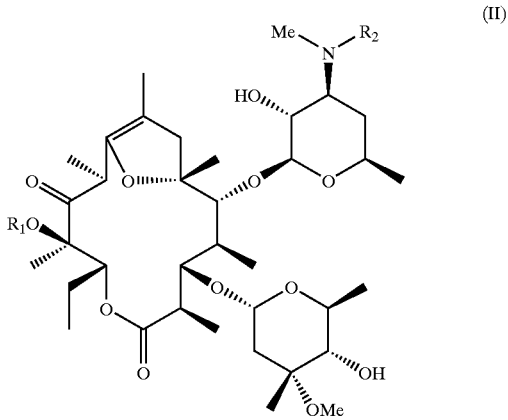

(II)

(wherein R₁ represents a hydrogen atom or a lower alkyl group, and R₂ represents a lower alkyl group), which comprises crystallizing a fumarate salt of the compound represented by Formula (II) from isopropanol to give a crystal of the fumarate salt of the compound, and recrystallizing the crystal from isopropanol and then from a mixed methanol/isopropanol solvent.

BEST MODE FOR CARRYING OUT THE INVENTION

The following terms used herein are intended to have the meanings shown below, unless otherwise specified.

A lower alkyl group refers to a linear or branched $C_1$–$C_6$ alkyl group, including a methyl group, an ethyl group, an n-propyl group, an isopropyl group, an n-butyl group, a sec-butyl group, a tert-butyl group, a pentyl group and a hexyl group.

The lower alkyl group in $R_1$ is preferably a methyl group, an ethyl group, an n-propyl group or an isopropyl group, and particularly preferably a methyl group.

The lower alkyl group in $R_2$ is preferably a methyl group, an ethyl group, an n-propyl group or an isopropyl group, and particularly preferably an isopropyl group.

A chloroformate refers to an alkyl chlorocarbonate, including methyloxycarbonyl chloride, ethyloxycarbonyl chloride, 2-phenylethyloxycarbonyl chloride, tert-butyloxycarbonyl chloride, vinyloxycarbonyl chloride, allyloxycarbonyl chloride, p-methoxybenzyloxycarbonyl chloride, p-nitrobenzyloxycarbonyl chloride and benzyloxycarbonyl chloride.

A carbamate group refers to an alkyl carbonate group, including a methyloxycarbonyl group, an ethyloxycarbonyl group, a 2-phenylethyloxycarbonyl group, a tert-butyloxycarbonyl group, a vinyloxycarbonyl group, an allyloxycarbonyl group, a p-methoxybenzyloxycarbonyl group, a p-nitrobenzyloxycarbonyl group and a benzyloxycarbonyl group. The carbamate group in $R_3$ and $R_4$ is preferably a benzyloxycarbonyl group, a p-methoxybenzyloxycarbonyl group or an allyloxycarbonyl group, and particularly preferably a benzyloxycarbonyl group.

Examples of alcohols include methanol, ethanol, n-propanol, i-propanol, n-butanol, sec-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol.

An alcohol-containing solvent refers to a solvent comprising one or more alcohols. Examples include isopropanol and a mixed methanol/isopropanol solvent.

"One-pot" means that in a series of reactions, each reaction product is provided for the next reaction without isolation and purification. The one-pot reaction defined here encompasses not only a series of reactions conducted in a single reaction vessel, but also a series of reactions conducted in a plurality of reaction vessels (e.g., by transferring the reaction mixture from one vessel to other) without isolation and purification. Preferably, the one-pot reaction is conducted in a single reaction vessel.

As used herein, "-fold amount" relative to a material is intended to mean a weight-to-weight ratio relative to the material. For example, 2-fold amount relative to a material means a 2:1 weight-to-weight ratio relative to the material. In a case where a target to be compared is a fluid such as a solvent, "-fold amount" relative to a material is intended to mean a volume-to-weight ratio of the fluid to the material. For example, 2-fold amount of a solvent relative to a material means a 2:1 volume-to-weight ratio of the solvent (e.g., 2 liter) to the material (e.g., 1 kg).

In turn, the preparation method of the present invention will be described below.

In one embodiment, the preparation method of the present invention comprises a first step of carbamating a compound represented by Formula (I) to give a compound represented by Formula (III), a second step of removing all carbamate groups from the compound represented by Formula (III) to give a compound represented by Formula (IV), a third step of alkylating the nitrogen atom at the 3'-position of the compound represented by Formula (IV) to give a compound represented by Formula (II), a fourth step of converting the compound represented by Formula (II) into a fumarate salt to give a fumarate salt of the compound represented by Formula (II), and a fifth step of recrystallizing the fumarate salt of the compound represented by Formula (II) to give a purified crystal of the fumarate salt of the compound represented by Formula (II). In another embodiment, the preparation method of the present invention comprises the first, second, third and fourth steps mentioned above. In another embodiment, the preparation method of the present invention comprises the first, second and third steps mentioned above. In another embodiment, the preparation method of the present invention comprises the first step mentioned above. In another embodiment, the preparation method of the present invention comprises the second step mentioned above. In another embodiment, the preparation method of the present invention comprises the fourth step mentioned above. In a final embodiment, the preparation method of the present invention comprises the fifth step mentioned above.

In the case of involving the first and second steps in the preparation method of the present invention, these first and second steps are preferably conducted in one-pot. Likewise, in the case of involving the second and third steps, these second and third steps are preferably conducted in one-pot. In the case of involving the third and fourth steps, these third and fourth steps are preferably conducted in one-pot. In the case of involving the fourth and fifth steps, these fourth and fifth steps are preferably conducted in one-pot.

An example of the preparation method of the present invention will be illustrated below.

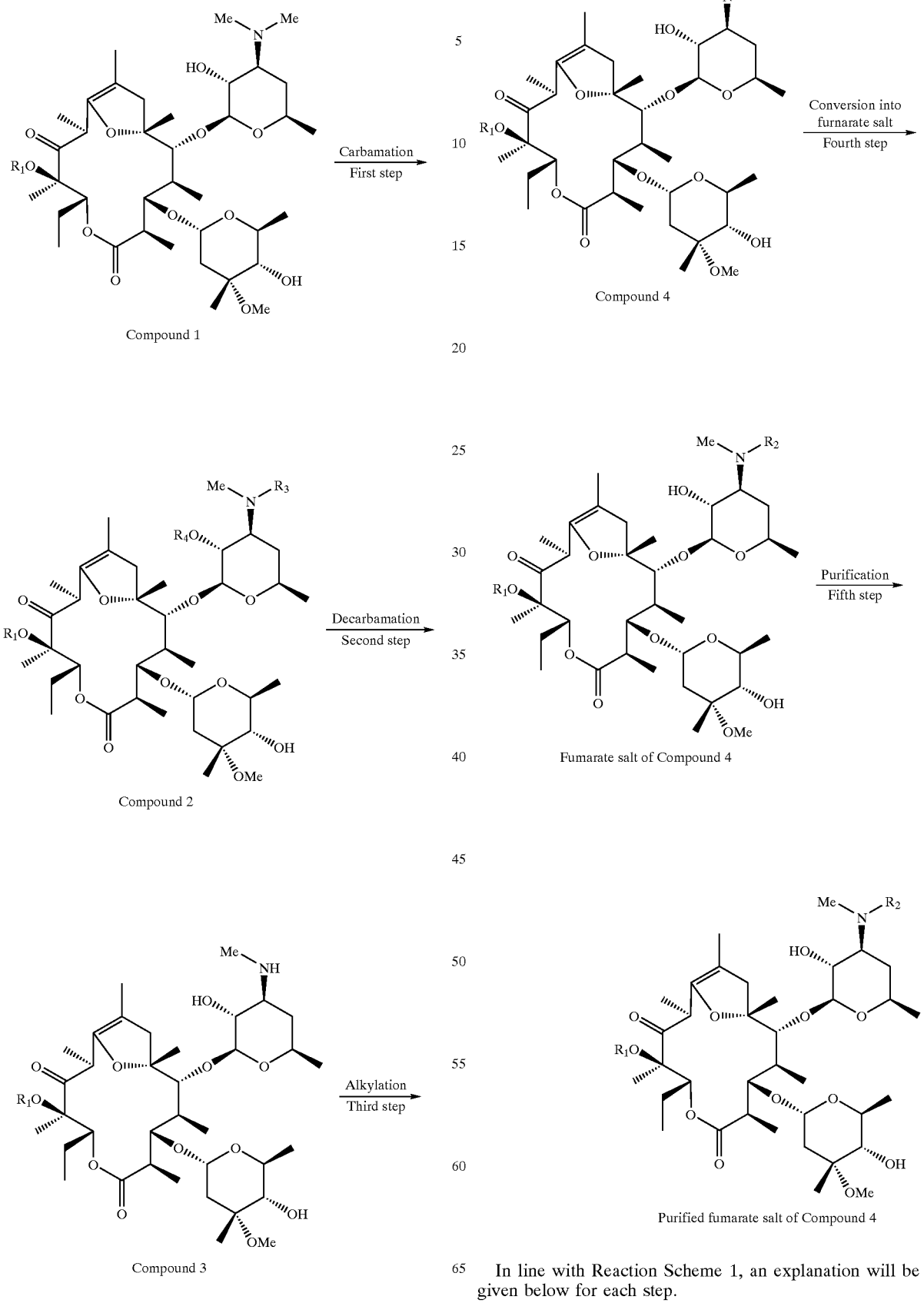
In line with Reaction Scheme 1, an explanation will be given below for each step.

First, Compound 1 as a compound represented by Formula (I) is reacted with a chloroformate under basic conditions to give Compound 2 as a compound represented by Formula (III) (first step). The chloroformate used in carbamation is preferably benzyloxycarbonyl chloride, p-methoxybenzyloxycarbonyl chloride or allyloxycarbonyl chloride, and particularly preferably benzyloxycarbonyl chloride.

Examples of a base available for use include inorganic bases such as sodium bicarbonate, potassium carbonate and sodium hydroxide, and tertiary amines such as triethylamine and diisopropylethylamine. Preferred are inorganic bases, more preferred are sodium bicarbonate and potassium carbonate, and particularly preferred is sodium bicarbonate.

Any solvent may be used as long as it does not affect the reaction, including aromatic hydrocarbon solvents, carboxylic esters and ethers. Preferred are carboxylic esters and ethers, and more preferred are carboxylic esters. A preferred aromatic hydrocarbon solvent is toluene. Examples of carboxylic esters include ethyl formate, methyl acetate, ethyl acetate, isopropyl acetate and ethyl propionate, with acetic esters being preferred and with ethyl acetate being more preferred. Preferred ethers are cyclic ethers. Examples of cyclic ethers include oxirane, tetrahydrofuran, tetrahydropyran and dioxane, with tetrahydrofuran being preferred. The solvent used for carbamation is preferably toluene, tetrahydrofuran or ethyl acetate, more preferably tetrahydrofuran or ethyl acetate, and particularly preferably ethyl acetate.

The reaction temperature usually ranges from about 0° C. to 120° C., preferably 20° C. to 110° C., more preferably 40° C. to 80° C., particularly preferably 45° C. to 70° C.

The reaction time usually ranges from about 0.5 to 12 hours, preferably 0.5 to 10 hours, more preferably 0.5 to 3 hours. In this step, the chloroformate is generally used in an amount of 5 to 15 equivalents, preferably 7 to 13 equivalents, more preferably 8 to 12 equivalents, particularly preferably 10 to 12 equivalents, relative to the compound represented by Formula (I).

In this step, the base is generally used in an amount of 5 to 18 equivalents, preferably 7 to 15 equivalents, more preferably 9 to 12 equivalents, relative to the compound represented by Formula (I).

All carbamate groups are removed from Compound 2 as a compound represented by Formula (III) to give Compound 3 as a compound represented by Formula (IV) (second step). Removal of carbamate groups is accomplished by a standard deprotection reaction. Examples of such a deprotection reaction include catalytic hydrogenation and acid treatment. Preferred are catalytic hydrogenation in the presence of a palladium-carbon catalyst, treatment with an organic acid such as formic acid, acetic acid, propionic acid, oxalic acid or fumaric acid, and treatment with an inorganic acid such as hydrochloric acid or phosphoric acid. Particularly preferred is catalytic hydrogenation in the presence of a palladium-carbon catalyst. In a case where a palladium-carbon catalyst is used in the deprotection reaction, this catalyst is generally used in a 0.01- to 1.0-fold amount, preferably in a 0.1- to 0.5-fold amount, more preferably in a 0.13- to 0.39-fold amount, relative to the compound represented by Formula (I) used in the first step. Catalytic hydrogenation is preferably performed under basic conditions. Examples of a base available for this purpose include inorganic bases such as sodium bicarbonate, potassium carbonate and sodium hydroxide, and tertiary amines such as triethylamine and diisopropylethylamine. Preferred are inorganic bases, more preferred are sodium bicarbonate and potassium carbonate, and particularly preferred is sodium bicarbonate.

As a hydrogen source, hydrogen, ammonium formate or the like may be used. In a case where hydrogen is used as a hydrogen source, catalytic hydrogenation may be performed under pressure, preferably at a pressure of about 0.01 to 1.0 MPa, more preferably 0.05 to 0.5 MPa. Any solvent may be used as long as it is inert to the reaction, preferably including alcohol solvents and ester solvents. More preferred are methanol, ethanol and ethyl acetate, and particularly preferred is methanol. The reaction temperature usually ranges from about 0° C. to 60° C., preferably 10° C. to 50° C., more preferably 20° C. to 40° C. The reaction time usually ranges from about 0.5 to 3 hours, preferably 1 to 2 hours.

The nitrogen atom at the 3'-position of the desosamine ring in Compound 3 as a compound represented by Formula (IV) is alkylated to give Compound 4 as a compound represented by Formula (II) (third step). Examples of an alkylating agent used for alkylation in the third step include alkyl halides, alkyl tosylates and alkyl mesylates, with alkyl halides being preferred. A preferred alkyl halide has an isopropyl group as its alkyl moiety. Examples of an isopropylating agent include isopropyl iodide, isopropyl methanesulfonate and isopropyl p-toluenesulfonate, with isopropyl iodide being preferred. Examples of a base available for use include organic bases (e.g., amines) and inorganic bases. Preferred are diisopropylethylamine, triethylamine, morpholine, piperidine, pyrrolidine and pyridine, and more preferred is triethylamine. Any solvent may be used as long as it is inert to the reaction. Preferred are aprotic polar solvents and alcohol solvents, and more preferred are dimethylimidazolidinone, dimethylformamide, acetonitrile and the like. The alkylating agent is generally used in an amount of 6 to 15 equivalents, preferably 7 to 13 equivalents, more preferably 8 to 12 equivalents, particularly preferably 8 to 10 equivalents, relative to the compound represented by Formula (I) used in the first step. The base is generally used in an amount of 5 to 15 equivalents, preferably 7 to 13 equivalents, more preferably 8 to 12 equivalents, relative to the compound represented by Formula (I). The solvent is generally used in a 2- to 12-fold amount, preferably in a 3- to 10-fold amount, more preferably in a 3- to 8-fold amount, particularly preferably in a 3- to 6-fold amount, relative to the compound represented by Formula (I) used in the first step. The reaction temperature usually ranges from about 0° C. to 130° C., preferably 50° C. to 100° C., more preferably 60° C. to 90° C. The reaction time usually ranges from about 3 hours to 10 days, preferably 5 to 10 hours.

Compound 4 as a compound represented by Formula (II) is converted into a fumarate salt to give a fumarate salt of Compound 4 as a fumarate salt of the compound represented by Formula (II) (fourth step).

Conversion into a fumarate salt is accomplished by a standard technique for salt formation. Examples of a solvent available for use include alcohol solvents, ether solvents, acetone and ethyl acetate, with alcohol solvents being preferred. Among these, preferred are methanol, ethanol and isopropanol, more preferred are methanol and isopropanol, and particularly preferred is isopropanol. These solvents may be used alone or in combination. In a case where fumaric acid is used for the conversion into a fumarate salt, fumaric acid is generally used in an amount of 0.3 to 2 equivalents, preferably 0.3 to 1 equivalent, more preferably 0.4 to 0.8 equivalents, particularly preferably 0.4 to 0.6 equivalents, relative to the compound represented by Formula (II). The reaction temperature usually ranges from about 20° C. to 100° C., preferably 0° C. to 90° C., more preferably 20° C. to 80° C. The reaction time usually ranges from about 1 to 6 hours, preferably 3 to 4 hours.

The fumarate salt of Compound 4 as a fumarate salt of the compound represented by Formula (II) is purified to give a purified fumarate salt of Compound 4 (fifth step).

A fumarate salt of the compound represented by Formula (II) is purified, as needed. Purification is preferably accomplished by recrystallization. Examples of a solvent for recrystallization include ester solvents which may contain water, alcohol solvents which may contain water, ether solvents which may contain water, and mixed solvents thereof. Preferred are isopropanol, a mixed methanol/isopropanol solvent and a mixed ethyl acetate/water solvent, and more preferred are isopropanol and a mixed methanol/isopropanol solvent. The mixing ratio between methanol and isopropanol preferably ranges from 10:90 to 50:50, more preferably 20:80 to 30:70. The mixing ratio between ethyl acetate and water preferably ranges from 99.5:0.5 to 95:5, more preferably 99:1 to 96:4, particularly preferably 98.5:1.5 to 97:3.

Preferably, the above recrystallization step is performed at decreasing temperature. It usually starts at a temperature of 10° C. to 100° C., preferably 10° C. to 90° C., more preferably 20° C. to 80° C., particularly preferably 70° C. to 80° C. The temperature usually decreases at a rate of 5° C./hour to 130° C./hour, preferably 10° C./hour to 120° C./hour, more preferably 10° C./hour to 50° C./hour, particularly preferably 10° C./hour to 30° C./hour. The temperature usually decreases to a final temperature of −10° C. to 0° C.

When recrystallization is performed for purification, it is preferably repeated twice or more. In such a case where recrystallization is repeated twice or more, the fumarate salt is preferably recrystallized from isopropanol and then from a mixed methanol/isopropanol solvent.

EXAMPLES

The present invention will be further described in the following Examples, which are not intended to limit the scope of the invention. In the following Examples, $^1$H-NMR data present characteristic peaks only. The conversion and purity were determined by high performance liquid chromatography (HPLC).

Example 1

Synthesis of Z Compound (Compound 6)

Ethyl acetate (63.1 kg) was added to Compound 5 (dihydroxy compound; 14 kg) and sodium bicarbonate (11.3 kg). After this mixture was heated to 55° C., benzyloxycarbonyl chloride (6.6 kg) was added and stirred for 1 hour. Additional benzyloxycarbonyl chloride (29.5 kg) was added and stirred for 1 hour, followed by cooling. As a result, the starting dihydroxy compound (Compound 5) and its reaction intermediate (Compound 5 protected with one benzyloxycarbonyl group) completely disappeared and they were each converted into the titled compound.

To this solution, pyridine (0.015 kg) was added and stirred for 0.5 hours. This procedure, where pyridine (0.015 kg) was added and stirred for 0.5 hours, was repeated 3 times more, followed by addition of additional pyridine (5.3 kg).

To this solution, water (70.0 kg) was added and stirred, followed by partition to remove the aqueous phase. Further, the organic phase was washed with saturated brine (70.0 kg) and concentrated under reduced pressure to give the titled compound as an oil.

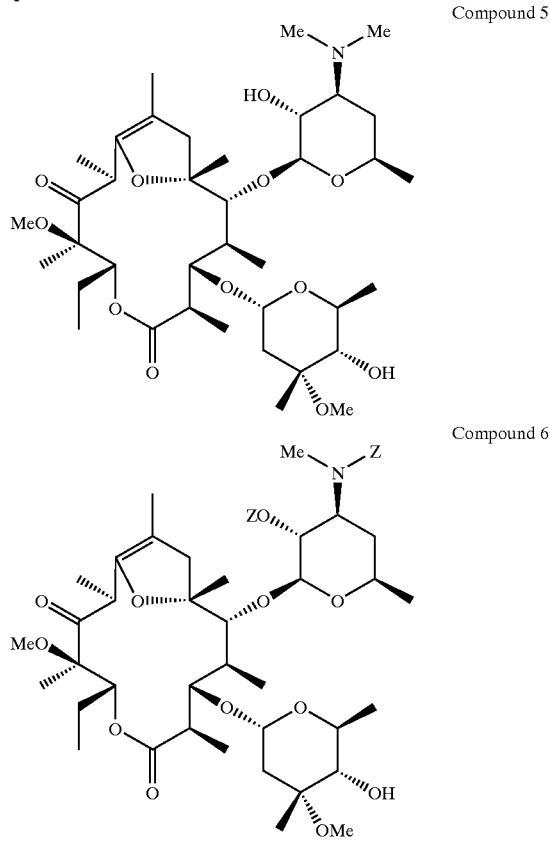

Example 2

Synthesis of Monomethyl Compound (Compound 7)

The compound prepared in Example 1 was used without isolation and purification. To this compound, methanol (88.5 kg), 10% palladium-carbon (3.6 kg) and sodium bicarbonate (16.2 kg) were added and stirred under a hydrogen atmosphere (0.1 to 0.4 MPa) for 1 hour at 25° C. to 50° C. As a result, the starting Z compound (Compound 6) and its reaction intermediate (Compound 6 lacking one benzyloxycarbonyl group by deprotection) completely disappeared and they were each converted into the titled compound. After the palladium-carbon was filtered off, the filtrate was concentrated under reduced pressure. The residue was dissolved in ethyl acetate (88.4 kg), to which saturated aqueous sodium bicarbonate (49.0 kg) was then added and stirred, followed by partition to remove the aqueous phase. The organic phase was then washed with saturated brine (49.0 kg) and concentrated under reduced pressure to give the titled compound as an oil.

Compound 7

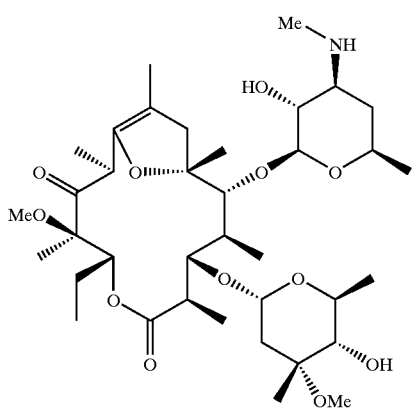

Example 3

Synthesis of Isopropyl Compound (Compound 8)

The compound prepared in Example 2 was used without isolation and purification. To this compound, 1,3-dimethyl-2-imidazolidinone (58.9 kg) was added. To this solution, triethylamine (19.5 kg) and isopropyl iodide (29.4 kg) were added at 75° C. and stirred with heating for 6 hours to convert 98% of the starting monomethyl compound (Compound 7) into the titled compound. After cooling to 30° C. or below, ethyl acetate (82.0 kg) and 25% aqueous ammonia (3.6 kg) were added. To this solution, water (70.0 kg) was further added and stirred, followed by partition to remove the aqueous phase. This procedure, where water was added and stirred, followed by partition to remove the aqueous phase, was repeated twice more. The resulting organic phase was concentrated under reduced pressure to give the titled compound.

Compound 8

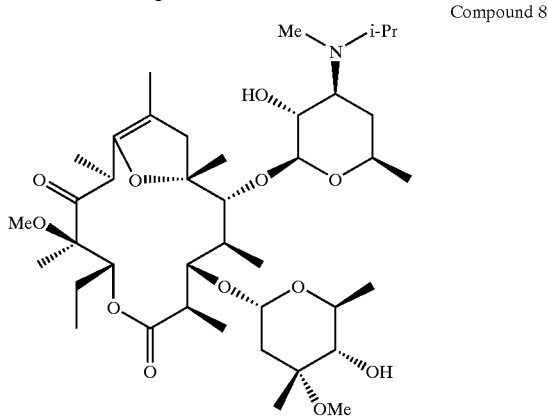

Example 4

Synthesis of Amo Compound (Fumarate Salt of Compound 8)

The compound prepared in Example 3 was used without isolation and purification. To this compound, fumaric acid (1.1 kg) and isopropanol (109.9 kg) were added and heated to 71° C., followed by cooling to 10° C. or below at a rate of 20° C./hour. The precipitated crystals were collected by filtration to give crystals of the titled compound (wet powders; calculated dry yield: 86.2%; purity: 92.21%). To the wet powders, isopropanol (106.0 kg) was added and heated to 71° C., followed by cooling to 10° C. or below at a rate of 20° C./hour. The precipitated crystals were collected by filtration to give crystals of the titled compound (wet powders; purity: 98.74%).

Example 5

Purification of Amo Compound (Fumarate Salt of Compound 8)

The crystals prepared in Example 4 were used without drying. To the crystals, methanol (2.5 volumes per calculated dry weight of the compound prepared in Example 4) and isopropanol (7.5 volumes per calculated dry weight of the compound prepared in Example 4) were added and heated to 60° C., followed by cooling to 0° C. or below at a rate of 20° C./hour. The precipitated crystals were collected by filtration to give crystals (wet powders) of the titled compound. The above procedure was repeated once again without drying the resulting crystals to give crystals of the titled compound (wet powders; purity: 99.44%).

Example 6

Synthesis of Z Compound (Compound 10)

Ethyl acetate (225 mL) was added to Compound 9 (dihydroxy compound; 45.0 g, 63.1 mmol) and sodium bicarbonate (37.1 g, 441.6 mmol). After this mixture was heated to 55° C., benzyloxycarbonyl chloride (21.5 g, 126.2 mmol) was added and stirred for 1 hour. As a result, the starting dihydroxy compound (Compound 9) and its reaction intermediate (Compound 9 protected with one benzyloxycarbonyl group) completely disappeared and they were each converted into the titled compound. Additional benzyloxycarbonyl chloride (96.9 g, 567.7 mmol) was added and stirred for 1 hour, followed by cooling.

To this reaction mixture, water (300 mL) was added and stirred, followed by partition to remove the aqueous phase. This procedure, where water (300 mL) was added and stirred, followed by partition to remove the aqueous phase, was repeated twice more. Further, the organic phase was washed with saturated brine (200 mL) and concentrated under reduced pressure to give the titled compound (140.3 g) as an oil.

Compound 9

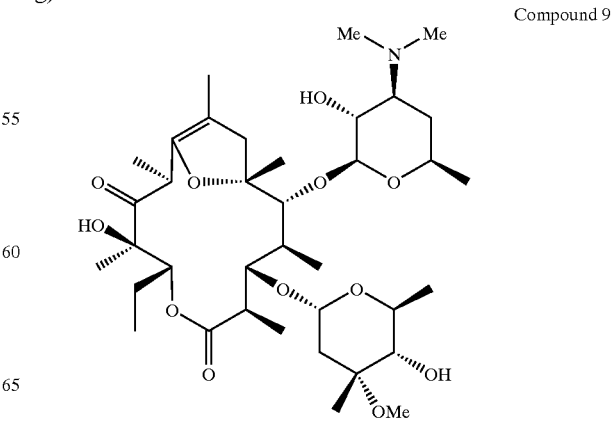

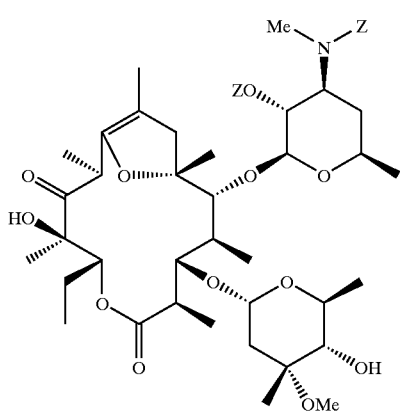

Compound 10

Example 7

Synthesis of Monomethyl Compound (Compound 11)

The compound prepared in Example 6 was used without isolation and purification. To this compound (20.4 g, 28.6 mmol), methanol (102 mL), 10% palladium-carbon (5.3 g) and sodium bicarbonate (24.0 g, 285.7 mmol) were added and stirred under a hydrogen atmosphere (0.1 to 0.4 MPa) for 1 hour at 25° C. to 50° C. As a result, the starting Z compound (Compound 10) and its reaction intermediate (Compound 10 lacking one benzyloxycarbonyl group by deprotection) completely disappeared and they were each converted into the titled compound. After the palladium-carbon was filtered off, the filtrate was concentrated under reduced pressure. The residue was dissolved in ethyl acetate (300 mL), to which water (200 mL) was then added and stirred, followed by partition to remove the aqueous phase. To this solution, additional water (200 mL) was added and stirred, followed by partition to remove the aqueous phase. Similarly, the organic phase was then washed with saturated brine (200 mL) and concentrated under reduced pressure to give the titled compound (26.3 g) as an oil.

Compound 11

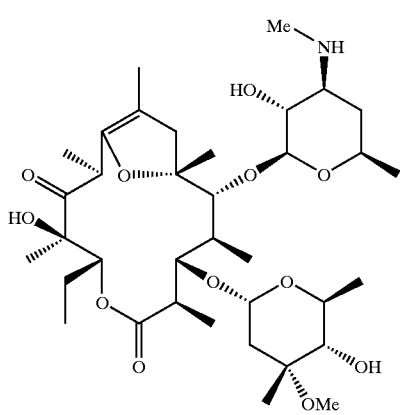

Example 8

Synthesis of Isopropyl Compound (Compound 12)

The compound (21.6 g, 30.8 mmol) prepared in Example 7 was used without isolation and purification. To this compound, 1,3-dimethyl-2-imidazolidinone (86 mL) was added. To this solution, triethylamine (31.1 g, 307.5 mmol) and isopropyl iodide (47.0 g, 276.8 mmol) were added at 75° C. and stirred with heating for 6 hours to convert 98% of the starting monomethyl compound (Compound 11) into the titled compound. After cooling to 30° C. or below, ethyl acetate (500 mL) and 25% aqueous ammonia (5.4 mL) were added. To this solution, water (300 mL) was further added and stirred, followed by partition to remove the aqueous phase. This procedure, where water (300 mL) was further added and stirred, followed by partition to remove the aqueous phase, was repeated 3 times. The organic phase was concentrated under reduced pressure to give the titled compound (22.1 g).

Compound 12

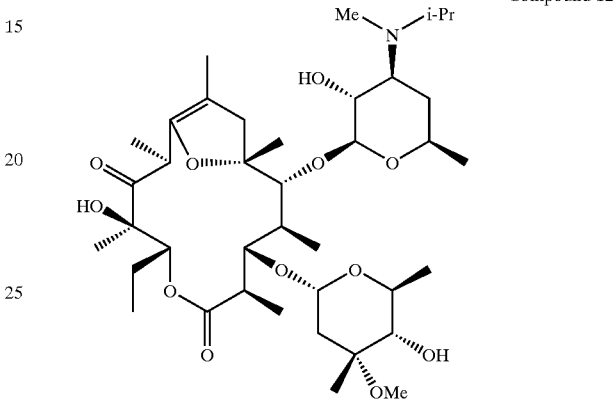

Example 9

Synthesis of Amo Compound (Fumarate Salt of Compound 12)

The compound prepared in Example 8 was used without isolation and purification. To this compound (17.0 g, 22.9 mmol), fumaric acid (1.3 g) and isopropanol (170 mL) were added and heated to 71° C., followed by cooling to 10° C. or below at a rate of 20° C./hour. The precipitated crystals were collected by filtration to give crystals (6.8 g) of amo compound (fumarate salt of Compound 12).

Example 10

Purification of Amo Compound (Fumarate Salt of Compound 12)

The crystals prepared in Example 9 were used without drying. To the crystals (6.59 g), methanol (8.2 mL) and isopropanol (24.8 mL) were added and heated to 60° C., followed by cooling to 0° C. or below at a rate of 20° C./hour. The precipitated crystals were collected by filtration to give crystals (4.83 g; purity: 98.77%) of amo compound (fumarate salt of Compound 12).

$^1$H-NMR(CDCl$_3$, ppm): 4.9–5.0(1H,dd), 4.8(1H,d), 4.4 (1H,dd), 3.9–4.1(2H,m) 3.8–3.9(2H,m), 3.5(1H,m), 3.3(3H, s), 3.1–3.2(1H,m), 2.9–3.1(2H,m), 2.3–2.8(6H,m), 2.2(3H, s), 1.5–2.1(8H,m), 1.0–1.5(34H,m), 0.9(3H,t)

Industrial Applicability

The preparation method of the present invention is industrially advantageous in (1) providing improved reaction efficiency and reduced reaction time, (2) allowing dramatic simplification of the process and saving the time and labor required for the process due to elimination of procedures such as solvent replacement, (3) reducing the risk of product decomposition during reaction, (4) reducing the content of

What is claimed is:

1. A method for preparing a fumarate salt of a compound represented by Formula (II):

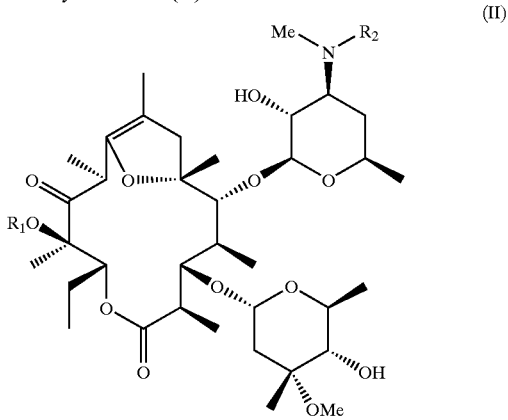

(wherein $R_1$ represents a hydrogen atom or a lower alkyl group, and $R_2$ represents a lower alkyl group), which comprises:

carbamating a compound represented by Formula (I):

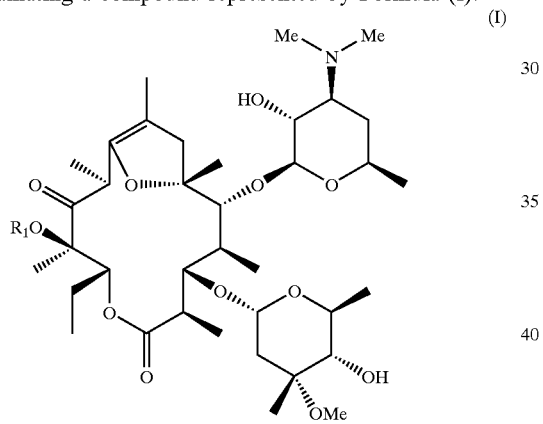

(wherein $R_1$ represents a hydrogen atom or a lower alkyl group) to give a compound represented by Formula (III):

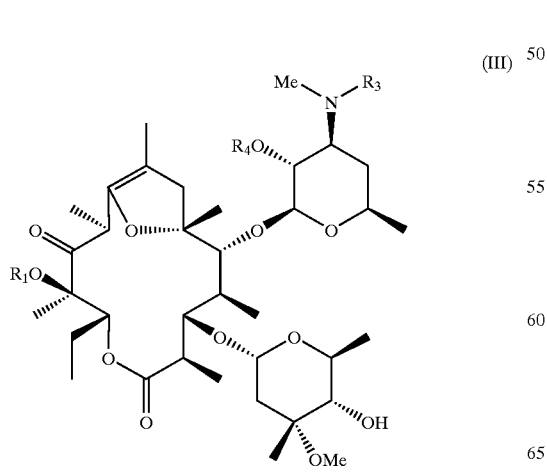

(wherein $R_1$ represents a hydrogen atom or a lower alkyl group, $R_3$ represents a carbamate group, and $R_4$ represents a hydrogen atom or a carbamate group);

removing all carbamate groups from the compound represented by Formula (III) to give a compound represented by Formula (IV):

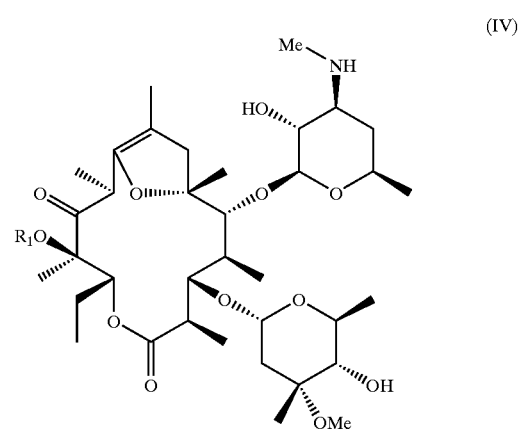

(wherein $R_1$ represents a hydrogen atom or a lower alkyl group);

alkylating the nitrogen atom at the 3'-position of the desosamine ring in the compound represented by Formula (IV) to give the compound represented by Formula (II); and converting the compound represented by Formula (II) into a fumarate salt;

wherein the compound represented by Formula (I) is carbamated in the presence of a cyclic ether or a carboxylic ester to give the compound represented by Formula (III).

2. A method for preparing a fumarate salt of a compound represented by Formula (II):

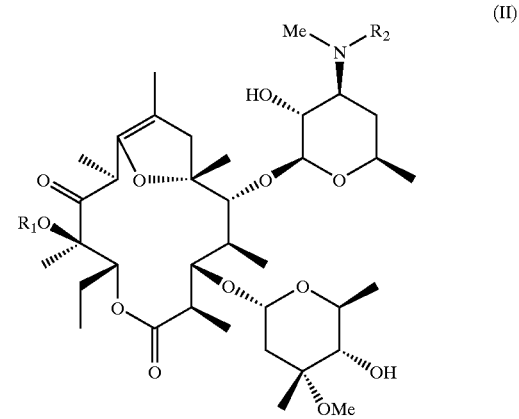

(wherein $R_1$ represents a hydrogen atom or a lower alkyl group, and $R_2$ represents a lower alkyl group), which comprises:

carbamating a compound represented by Formula (I):

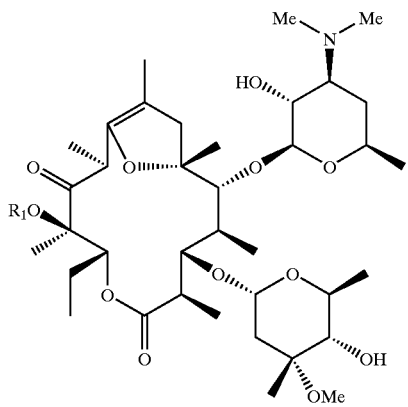

(wherein $R_1$ represents a hydrogen atom or a lower alkyl group) to give a compound represented by Formula (III):

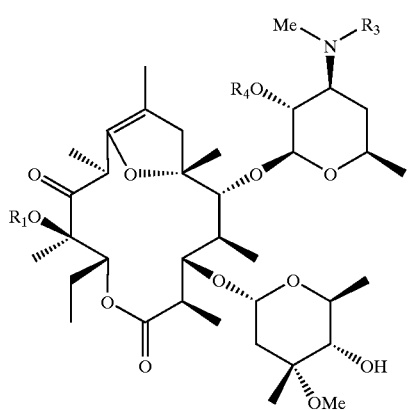

(wherein $R_1$ represents a hydrogen atom or a lower alkyl group, $R_3$ represents a carbamate group, and $R_4$ represents a hydrogen atom or a carbamate group);

removing all carbamate groups from the compound represented by Formula (III) to give a compound represented by Formula (IV):

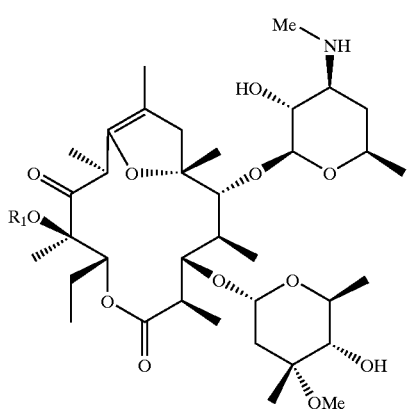

(wherein $R_1$ represents a hydrogen atom or a lower alkyl group);

alkylating the nitrogen atom at the 3'-position of the desosamine ring in the compound represented by Formula (IV) to give the compound represented by Formula (II); and converting the compound represented by Formula (II) into a fumarate salt;

wherein the carbamate groups of the compound represented by Formula (III) are removed in the presence of sodium bicarbonate to give the compound represented by Formula (IV).

3. A method for preparing a crystal of a fumarate salt of a compound represented by Formula (II):

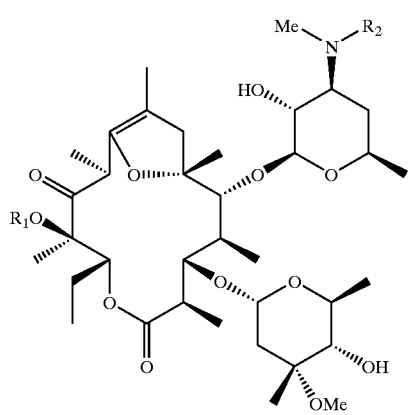

(wherein $R_1$ represents a hydrogen atom or a lower alkyl group, and $R_2$ represents a lower alkyl group), which comprises:

carbamating a compound represented by Formula (I):

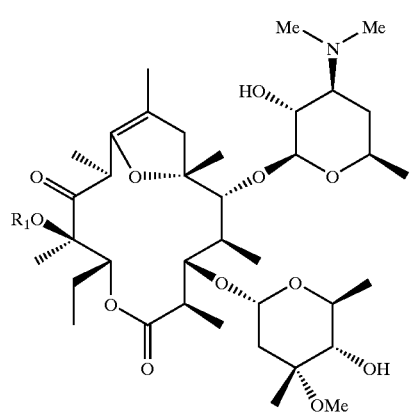

(wherein $R_1$ represents a hydrogen atom or a lower alkyl group) in the presence of a cyclic ether or a carboxylic ester to give a compound represented by Formula (III):

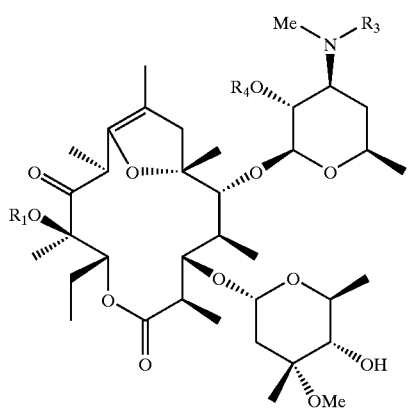

(III)

(wherein $R_1$ represents a hydrogen atom or a lower alkyl group, $R_3$ represents a carbamate group, and $R_4$ represents a hydrogen atom or a carbamate group);
removing all carbamate groups from the compound represented by Formula (III):

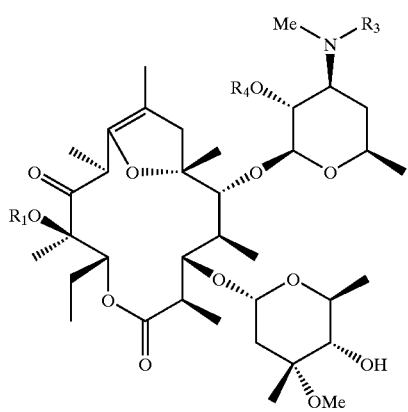

(III)

(wherein $R_1$ represents a hydrogen atom or a lower alkyl group, $R_3$ represents a carbamate group, and $R_4$ represents a hydrogen atom or a carbamate group) in the presence of sodium bicarbonate to give a compound represented by Formula (IV):

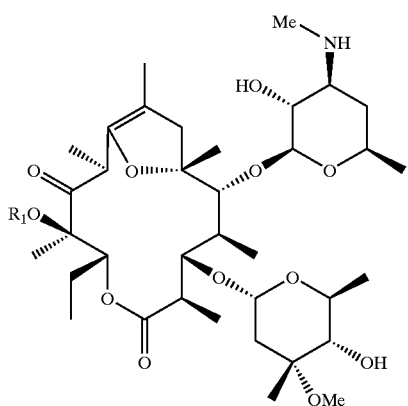

(IV)

(wherein $R_1$ represents a hydrogen atom or a lower alkyl group);
crystallizing a fumarate salt of the compound represented by Formula (II) from isopropanol to give a crystal of the fumarate salt of the compound; and recrystallizing the crystal from isopropanol and then from a mixed methanol/isopropanol solvent.

4. A method for preparing a compound represented by Formula (III):

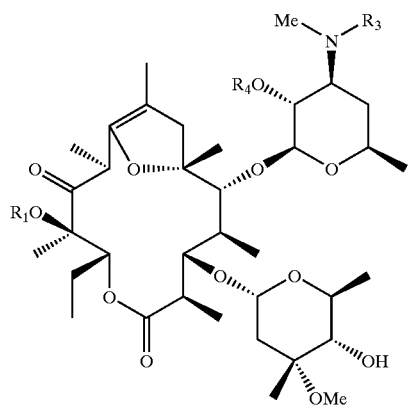

(III)

(wherein $R_1$ represents a hydrogen atom or a lower alkyl group, $R_3$ represents a carbamate group, and $R_4$ represents a hydrogen atom or a carbamate group), which comprises carbamating a compound represented by Formula (I):

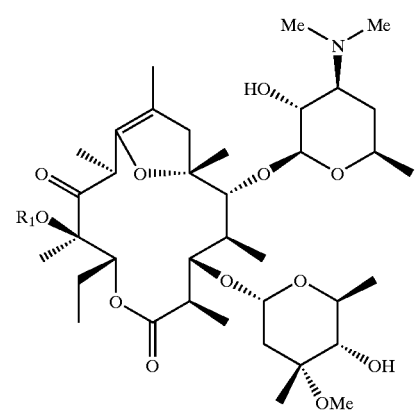

(I)

(wherein $R_1$ represents a hydrogen atom or a lower alkyl group) in the presence of a cyclic ether or a carboxylic ester.

5. A method for preparing a compound represented by Formula (IV):

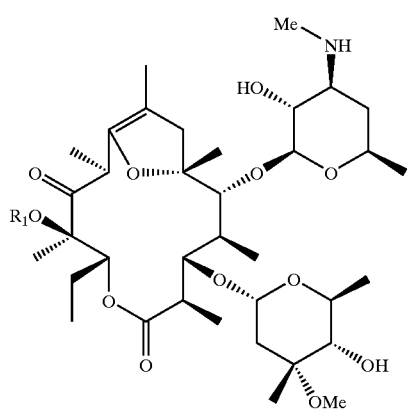

(IV)

(wherein $R_1$ represents a hydrogen atom or a lower alkyl group), which comprises removing all carbamate groups from a compound represented by Formula (III):

(III)

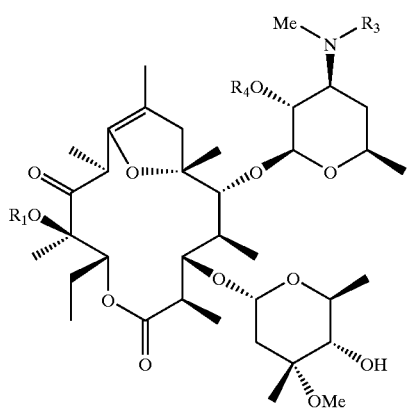

(wherein R₁ represents a hydrogen atom or a lower alkyl group, R₃ represents a carbamate group, and R₄ represents a hydrogen atom or a carbamate group) in the presence of sodium bicarbonate.

6. A method for preparing a crystal of a fumarate salt of a compound represented by Formula (II):

(II)

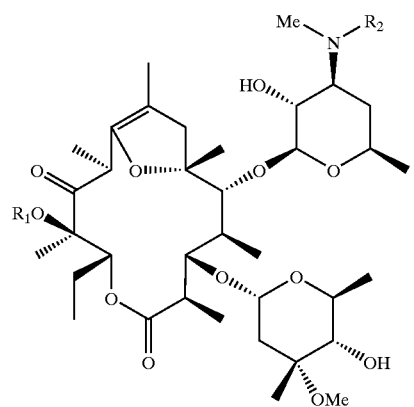

(wherein R₁ represents a hydrogen atom or a lower alkyl group, and R₂ represents a lower alkyl group), which comprises crystallizing a fumarate salt of the compound represented by Formula (II) from a single solvent of isopropanol.

7. A method for preparing a crystal of a fumarate salt of a compound represented by Formula (II):

(II)

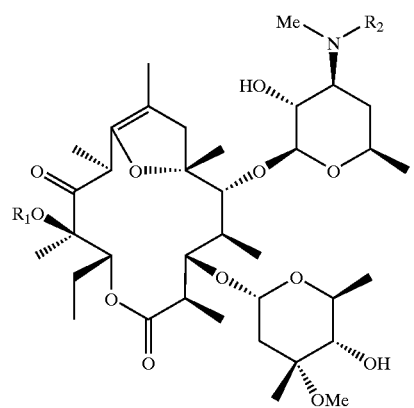

(wherein R₁ represents a hydrogen atom or a lower alkyl group, and R₂ represents a lower alkyl group), which comprises recrystallizing a crystal of a fumarate salt of the compound represented by Formula (II) from a single solvent of isopropanol.

8. A method for preparing a crystal of a fumarate salt of a compound represented by Formula (II):

(II)

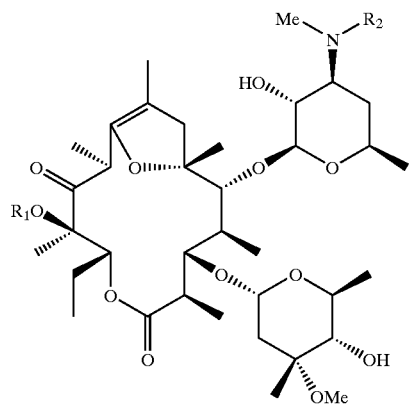

(wherein R₁ represents a hydrogen atom or a lower alkyl group, and R₂ represents a lower alkyl group), which comprises recrystallizing a crystal of a fumarate salt of the compound represented by Formula (II) from a single solvent of isopropanol and then from a mixed methanol/isopropanol solvent.

9. A method for preparing a crystal of a fumarate salt of a compound represented by Formula (II):

(II)

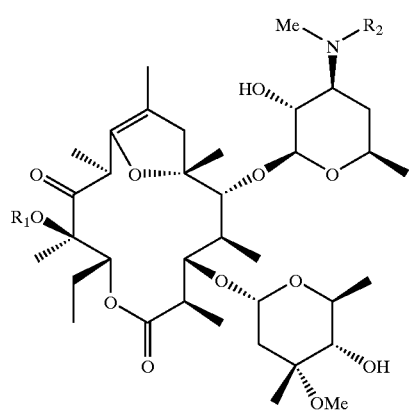

(wherein R₁ represents a hydrogen atom or a lower alkyl group, and R₂ represents a lower alkyl group), which comprises crystallizing a fumarate salt of the compound represented by Formula (II) from isopropanol to give a crystal of the fumarate salt of the compound, and recrystallizing the crystal from a single solvent of isopropanol and then from a mixed methanol/isopropanol solvent.

10. The method according to claim 1 or 3, wherein the cyclic ether or carboxylic ester is a carboxylic ester.

11. The method according to claim 10, wherein the carboxylic ester is an acetic ester.

12. The method according to claim 10, wherein the carboxylic ester is ethyl acetate.

13. The method according to any one of claims 1, 2 and 3, wherein the fumarate salt of the compound represented by Formula (II):

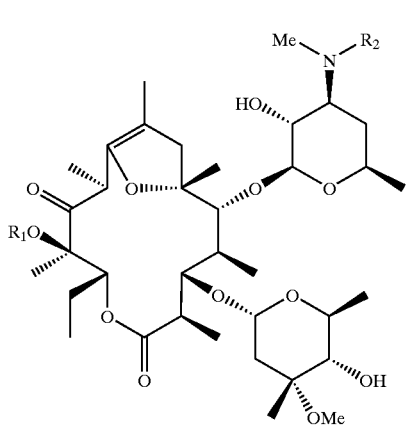

(II)

(wherein R₁ represents a hydrogen atom or a lower alkyl group, and R₂ represents a lower alkyl group) is crystallized at decreasing temperature.

14. The method according to claim 13, wherein the temperature decreases at a rate of 10° C./hour to 120° C./hour.

15. The method according to any one of claims 1, 2 and 3, wherein the crystal of the fumarate salt of the compound represented by Formula (II):

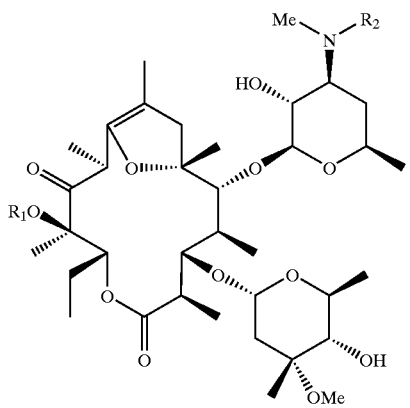

(II)

(wherein R₁ represents a hydrogen atom or a lower alkyl group, and R₂ represents a lower alkyl group) is recrystallized at decreasing temperature.

16. The method according to claim 15, wherein the temperature decreases at a rate of 10° C./hour to 120° C./hour.

17. The method according to claim 6, wherein the fumarate salt of the compound represented by Formula (II):

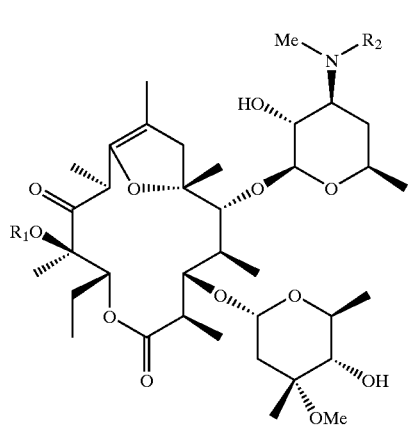

(II)

(wherein R₁ represents a hydrogen atom or a lower alkyl group, and R₂ represents a lower alkyl group) is crystallized at decreasing temperature.

18. The method according to claim 17, wherein the temperature decreases at a rate of 10° C./hour to 120° C./hour.

19. The method according to claim 9, wherein the fumarate salt of the compound represented by Formula (II):

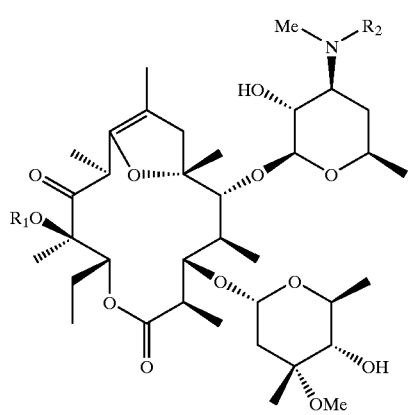

(II)

(wherein R₁ represents a hydrogen atom or a lower alkyl group, and R₂ represents a lower alkyl group) is crystallized at decreasing temperature.

20. The method according to claim 19, wherein the temperature decreases at a rate of 10° C./hour to 120° C./hour.

21. The method according to any one of claims 7–9 and 19–20, wherein the crystal of the fumarate salt of the compound represented by Formula (II):

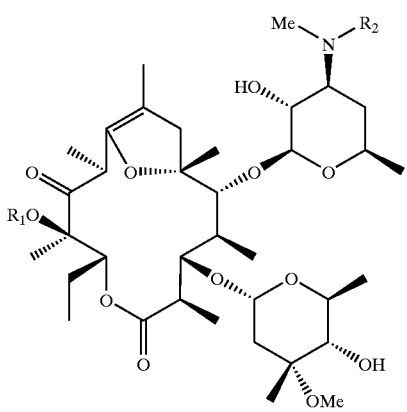

(II)

(wherein $R_1$ represents a hydrogen atom or a lower alkyl group, and $R_2$ represents a lower alkyl group) is recrystallized at decreasing temperature.

22. The method according to claim 21, wherein the temperature decreases at a rate of 10° C./hour to 120° C./hour.

23. The method according to any one of claims 1, 2 and 3, wherein $R_3$ and/or $R_4$ is a benzyloxycarbonyl group.

24. The method according to any one of claims 1, 2, 3 and 6–9, wherein $R_1$ is a methyl group.

25. The method according to any one of claims 1, 2 and 6–9, wherein $R_1$ is a methyl group and $R_2$ is an isopropyl group.

* * * * *